United States Patent
Kogane

(10) Patent No.: US 8,400,499 B2
(45) Date of Patent: Mar. 19, 2013

(54) ENDOSCOPE DEVICE, CAMERA DEVICE FOR ENDOSCOPE, AND DEFOGGING METHOD

(75) Inventor: Haruo Kogane, Kanagawa (JP)

(73) Assignee: Panasonic Corporation, Osaka (JP)

( * ) Notice: Subject to any disclaimer, the term of this patent is extended or adjusted under 35 U.S.C. 154(b) by 525 days.

(21) Appl. No.: 12/673,270

(22) PCT Filed: Sep. 4, 2008

(86) PCT No.: PCT/JP2008/002441
§ 371 (c)(1),
(2), (4) Date: Feb. 12, 2010

(87) PCT Pub. No.: WO2009/066407
PCT Pub. Date: May 28, 2009

(65) Prior Publication Data
US 2011/0211052 A1    Sep. 1, 2011

(30) Foreign Application Priority Data

Nov. 21, 2007    (JP) .................................. 2007-301459

(51) Int. Cl.
A62B 1/04    (2006.01)
H04N 9/47   (2006.01)
A61B 1/12    (2006.01)
G06K 9/00   (2006.01)

(52) U.S. Cl. .............. 348/65; 348/77; 348/78; 600/157; 382/100

(58) Field of Classification Search .................... 348/65, 348/77, 78; 600/101–183; 382/100
See application file for complete search history.

(56) References Cited

U.S. PATENT DOCUMENTS

| | | | | |
|---|---|---|---|---|
| 4,618,884 A * | 10/1986 | Nagasaki | ........................ | 348/65 |
| 4,870,950 A * | 10/1989 | Kanbara et al. | ................ | 600/109 |
| 2003/0225332 A1* | 12/2003 | Okada et al. | .................. | 600/439 |
| 2005/0197533 A1* | 9/2005 | May et al. | ...................... | 600/164 |
| 2005/0203418 A1* | 9/2005 | Yamada et al. | ............... | 600/466 |
| 2005/0228275 A1* | 10/2005 | Kawashima | .................. | 600/437 |
| 2007/0195425 A1* | 8/2007 | Arai | ............................. | 359/687 |
| 2008/0319266 A1* | 12/2008 | Poll et al. | ...................... | 600/157 |

FOREIGN PATENT DOCUMENTS

| | | |
|---|---|---|
| JP | 10-192245 A | 7/1998 |
| JP | 2000-300513 A | 10/2000 |
| JP | 2003-116789 A | 4/2003 |
| JP | 2004-105743 A | 4/2004 |
| JP | 2006-055275 A | 3/2006 |

OTHER PUBLICATIONS

International Search Report for PCT/JP2008/002441.

* cited by examiner

*Primary Examiner* — Sath V Perungavoor
*Assistant Examiner* — Xiolan Xu
(74) *Attorney, Agent, or Firm* — Pearne & Gordon LLP

(57) ABSTRACT

An endoscope apparatus (1) includes a rigid scope portion (2) having an imaging window (5) at a front end thereof; a camera unit portion (3) mounted to a root end of the rigid scope portion (2); and a vibration generating device (4) mounted to the camera unit portion (3). The camera unit portion (3) can obtain an image of the inside of a body cavity through the imaging window (5). The vibration generating device (4) provides vibration to the rigid scope portion (2) through the camera unit portion (3) to defog the imaging window (5). This can provide an endoscope apparatus that can reduce the cost and size of a scope portion and has a high defogging effect.

12 Claims, 2 Drawing Sheets

ENDOSCOPE DEVICE, CAMERA DEVICE FOR ENDOSCOPE, AND DEFOGGING METHOD

TECHNICAL FIELD

The present invention relates to an endoscope apparatus having a defogging function.

BACKGROUND ART

Generally, a cover glass is mounted to a front end of an insertion portion (scope portion) of an endoscope apparatus, and an image of the inside of a body cavity is obtained through the cover glass. When the insertion portion of the endoscope apparatus is inserted into the body cavity, condensation may cause fogging of the cover glass. The fogging of the cover glass prevents a satisfactory image of the inside of the body cavity from being obtained. However, if the insertion portion is withdrawn from the body cavity to defog the cover glass during surgery, surgery efficiency is reduced.

Thus, a conventional endoscope apparatus has been known having a function of defogging a cover glass with an insertion portion being inserted into a body cavity during surgery. In the conventional endoscope apparatus, an ultrasound transducer is provided near the cover glass at a front end of the insertion portion, and the ultrasound transducer provides ultrasound vibration to the cover glass to defog the cover glass. For example, Japanese Patent Laid-Open No. 2006-55275 discloses such an endoscope apparatus.

However, the conventional endoscope apparatus requires space for providing the ultrasound transducer at the front end of the insertion portion, thereby preventing a reduction in size of the insertion portion. For providing the ultrasound transducer at the front end of the insertion portion, a wire needs to be passed through the insertion portion to supply or control electric power. However, this requires measures to prevent leakage of electricity from the insertion portion in the body cavity, thereby increasing the cost and size of the insertion portion of the endoscope apparatus. The ultrasound transducer generates relatively weak vibration, and even if the ultrasound transducer is placed near the cover glass, an insufficient defogging effect of the cover glass is sometimes obtained.

Also, the insertion portion of the conventional endoscope apparatus is a so-called exclusive component into which the ultrasound transducer is incorporated. Thus, for example, an endoscope apparatus including a replaceable insertion portion according to the condition or purpose of use sometimes includes an exclusive insertion portion having a defogging function and also a general insertion portion having no defogging function. In such a case, the exclusive insertion portion sometimes needs to be selected due to the need for the defogging function, though the general insertion portion should be selected according to the condition of use. In this manner, the conventional endoscope apparatus has low flexibility in selection of the insertion portion of the endoscope apparatus.

DISCLOSURE OF THE INVENTION

Problems to be Solved by the Invention

The present invention is achieved under the above described background. The present invention has an object to provide an endoscope apparatus that can reduce the cost and size of a scope portion and has a high defogging effect.

Means for Solving the Problems

An aspect of the present invention provides an endoscope apparatus including: a rigid scope portion having an imaging window at a front end thereof; a camera unit portion that is mounted to a root end of the rigid scope portion and has an image pickup portion that can obtain an image through the imaging window; and a vibration generating device that is mounted to the camera unit portion and provides vibration to the rigid scope portion through the camera unit portion.

Another aspect of the present invention provides an endoscope camera apparatus used in the above described endoscope apparatus, wherein the endoscope camera apparatus is mounted to a root end of a rigid scope portion, and a vibration generating device can be mounted to the endoscope camera apparatus.

A further aspect of the present invention provides a defogging method of an endoscope apparatus used in an endoscope apparatus including: a rigid scope portion having an imaging window at a front end thereof; a camera unit portion that is mounted to a root end of the rigid scope portion and has an image pickup portion that can obtain an image through the imaging window; and a vibration generating device mounted to the camera unit portion, wherein the vibration generating device provides vibration to the rigid scope portion through the camera unit portion to defog the imaging window.

As described below, the present invention includes other aspects. Thus, the disclosure of the invention is intended to provide a part of the aspects of the present invention, and not intended to limit the scope of the invention herein described and claimed.

Figure 1:
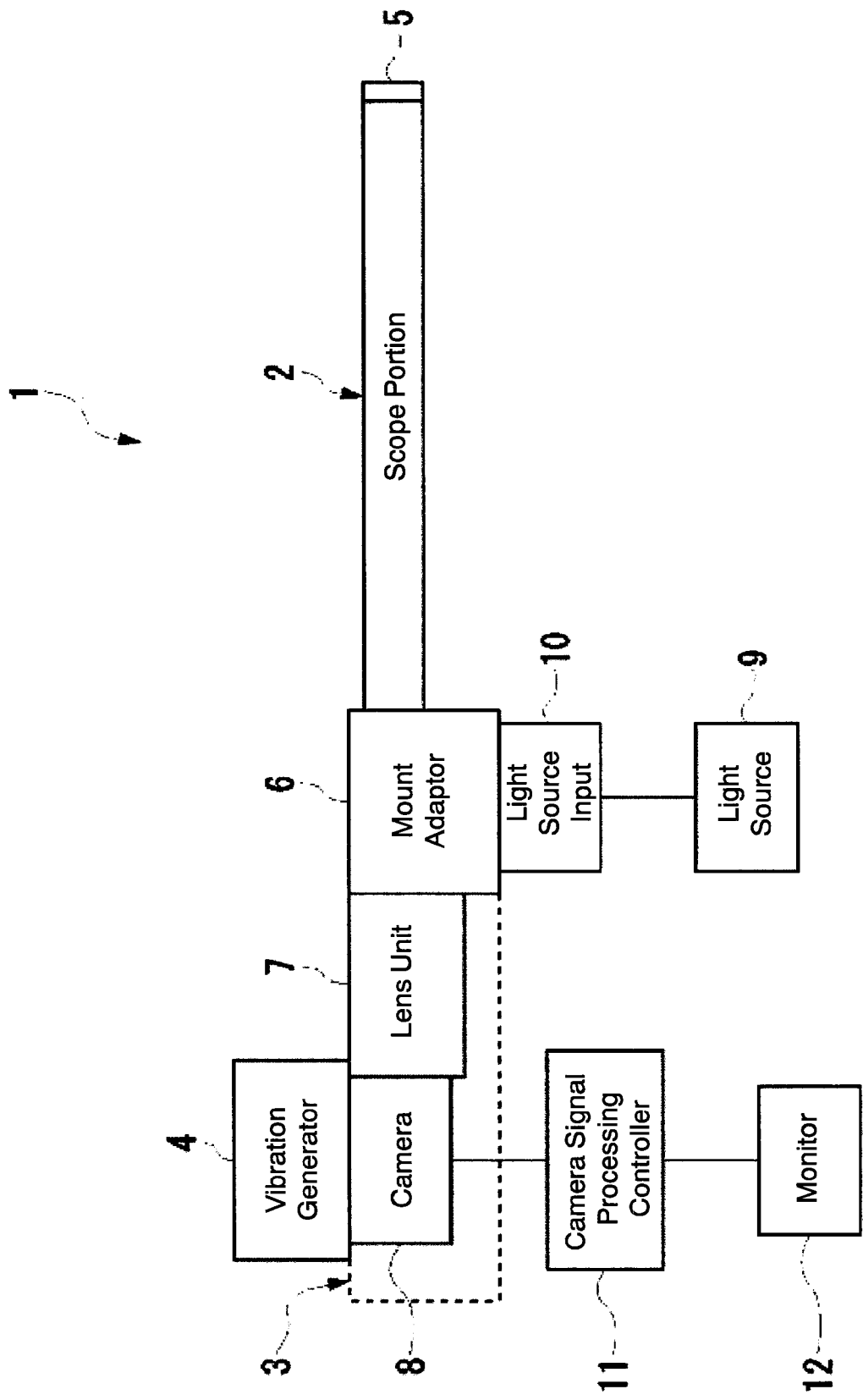
FIG. 1 is a block diagram of an endoscope apparatus according to an embodiment of the present invention.

DESCRIPTION OF SYMBOLS 1 endoscope apparatus
2 scope portion
3 camera unit portion
4 vibration generating device
5 imaging window
7 lens unit
8 camera portion
11 camera signal processing control portion
13 belt

BEST MODE FOR CARRYING OUT THE INVENTION

Now, the detailed description of the present invention will be described. The detailed description and the accompanying drawings do not limit the invention. Instead, the scope of the invention is defined by the appended claims.

An endoscope apparatus of the present invention includes: a rigid scope portion having an imaging window at a front end thereof; a camera unit portion that is mounted to a root end of the rigid scope portion and has an image pickup portion that can obtain an image through the imaging window; and a vibration generating device that is mounted to the camera unit portion and provides vibration to the rigid scope portion through the camera unit portion.

With this configuration, when the vibration generating device mounted to the camera unit portion generates vibration, the vibration is transmitted to the imaging window through the rigid scope portion to defog the imaging window. Thus, there is no need for providing a vibration generating device in a scope portion as in a conventional example, thereby reducing the size of the scope portion. Also, there is no need for passing a wire through the scope portion and for providing measures to prevent leakage of electricity as in the conventional example. This can reduce the cost and size of the scope portion. The vibration generating device is mounted to the camera unit portion, and thus the vibration generating device can easily generate strong vibration to provide a sufficient defogging effect.

The endoscope apparatus of the present invention may have a configuration including a vibration shake correction portion that corrects vibration shake of an image obtained by the image pickup portion while the vibration generating device is providing vibration to the rigid scope portion.

With this configuration, vibration shake of the obtained image that occurs while the vibration generating device is generating vibration is corrected. This allows quick confirmation of whether defogging is completed or not, thereby increasing surgery efficiency.

An endoscope camera apparatus of the present invention is used in the above described endoscope apparatus and mounted to a root end of a rigid scope portion, and a vibration generating device can be mounted to the endoscope camera apparatus.

Also with this configuration, as described above, when the vibration generating device mounted to the endoscope camera apparatus generates vibration, the vibration is transmitted to the imaging window through the rigid scope portion to defog the imaging window. Thus, there is no need for providing a vibration generating device in a scope portion as in the conventional example, thereby reducing the size of the scope portion. Also, there is no need for passing a wire through the scope portion and for providing measures to prevent leakage of electricity as in the conventional example. This can reduce the cost and size of the scope portion. The vibration generating device is mounted to the endoscope camera apparatus, and thus the vibration generating device can easily generate strong vibration to provide a sufficient defogging effect.

A defogging method of an endoscope apparatus of the present invention is used in an endoscope apparatus including: a rigid scope portion having a imaging window at a front end thereof; a camera unit portion that is mounted to a root end of the rigid scope portion and has an image pickup portion that can obtain an image through the imaging window; and a vibration generating device mounted to the camera unit portion, wherein the vibration generating device provides vibration to the rigid scope portion through the camera unit portion to defog the imaging window.

By providing the vibration generating device on the camera unit portion, the present invention can reduce the cost and size of the scope portion and has a high defogging effect.

Now, an endoscope apparatus according to an embodiment of the present invention will be described with reference to the drawings. In this embodiment, an endoscope apparatus used as a laparoscope for observing the inside of an abdominal cavity is exemplified.

Figure 2:
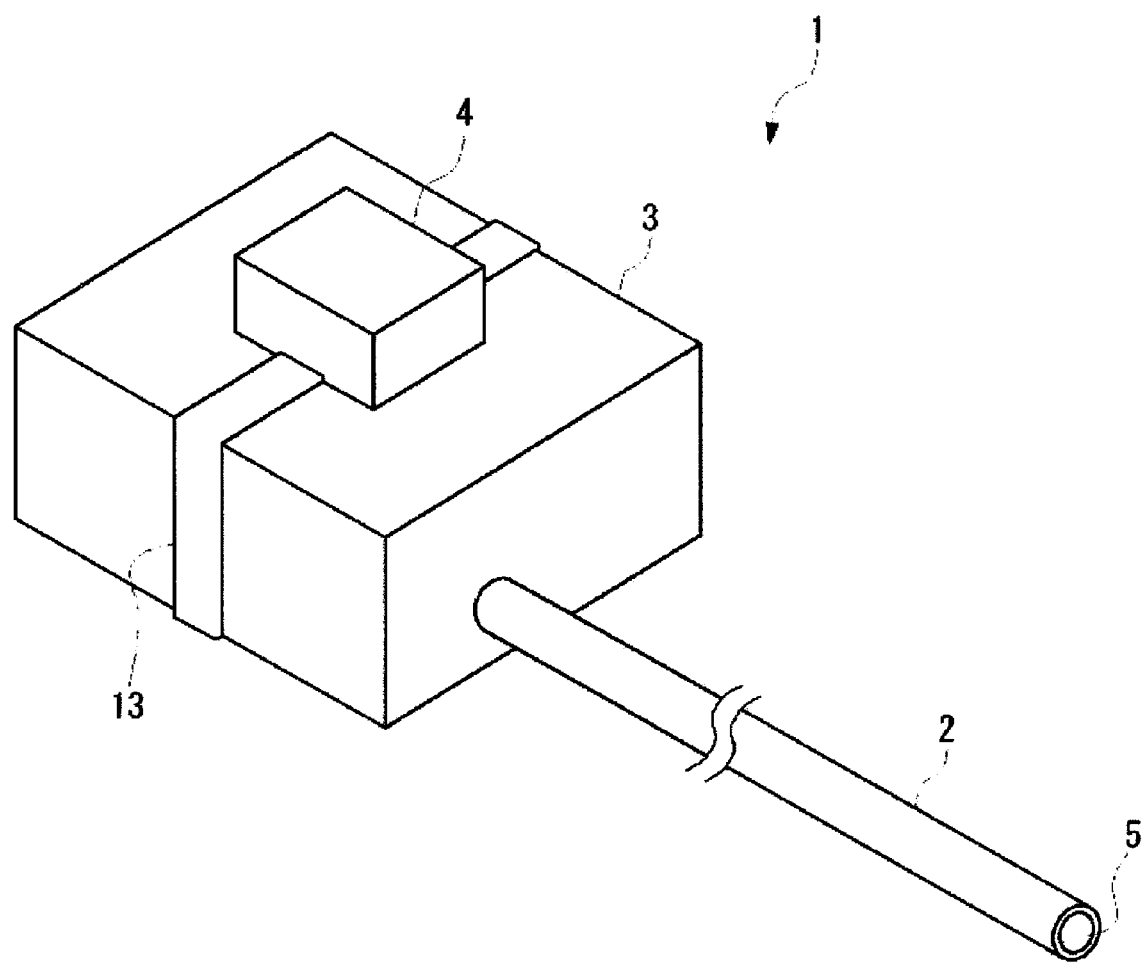
FIG. 2 is a simplified perspective view of the endoscope apparatus according to the embodiment of the present invention.

An endoscope apparatus according to the embodiment of the present invention is shown in FIGS. 1 and 2. FIG. 1 is a block diagram of the endoscope apparatus according to this embodiment, and FIG. 2 is a simplified perspective view of the endoscope apparatus.

As shown in FIGS. 1 and 2, the endoscope apparatus 1 includes a scope portion 2 inserted into an abdominal cavity, a camera unit portion 3 to which the scope portion 2 is mounted, and a vibration generating device 4 mounted to the camera unit portion 3. The camera unit portion 3 may be referred to as an endoscope camera apparatus.

The scope portion 2 is constituted by a bundle of optical fibers (not shown) so as to guide light from a root end to a front end. An imaging window 5 is provided at the front end of the scope portion 2. The imaging window 5 is formed of transparent optical glass or optical plastic.

The scope portion 2 has sufficient rigidity to transmit vibration, and the scope portion 2 may be referred to as a rigid scope portion. When the vibration generating device 4 generates vibration, the scope portion 2 vibrates at its natural frequency. Though not shown, the scope portion 2 may be covered with a plurality of joints whose directions can be freely changed within such a range that vibration can be transmitted, and the scope portion 2 may have flexibility in shape.

The camera unit portion 3 includes a mount adaptor 6 for mounting the scope portion 2, a lens unit 7 constituted by a plurality of lenses, and a camera portion 8 having an image pickup device such as a CCD or a CMOS. The image pickup device corresponds to an image pickup portion of the present invention.

In the endoscope apparatus 1 of this embodiment, various scope portions 2 can be removably mounted to the camera unit portion 3 via the mount adaptor 6. In the endoscope apparatus 1, positions of the plurality of lenses of the lens unit 7 are moved to allow focus adjustment or scaling.

The endoscope apparatus 1 also includes a light source 9 and a light source input portion 10. The light source 9 is connected to the mount adaptor 6 via the light source input portion 10. As the light source 9, for example, a halogen light is used. The light source input portion 10 includes a diaphragm spring (not shown) therein and has a function of modulating light from the light source 9.

The endoscope apparatus 1 includes a camera signal processing control portion 11 and a monitor 12. When the camera portion 8 obtains an image, the camera portion 8 outputs a camera signal. The camera signal processing control portion 11 performs signal processing of the camera signal, and the monitor 12 displays an image.

The vibration generating device 4 includes a vibration motor (not shown) therein. The vibration motor has a weight with an offset center of gravity mounted to a motor shaft, and generates vibration by rotating the motor shaft. The vibration motor is an example of a vibration generation mechanism, and the scope of the present invention is not limited thereto.

The vibration generating device 4 is removably mounted to the camera unit portion 3. FIG. 2 shows an example in which the vibration generating device 4 is secured to a casing of the camera unit portion 3 by a belt 13, but a mounting mechanism of the vibration generating device 4 is not limited thereto.

The endoscope apparatus 1 includes a vibration shake correction function. In this embodiment, the camera signal processing control portion 11 performs image processing for correcting vibration shake to electronically correct vibration shake. For example, vibration shake is electronically corrected by image processing such as electronic zoom or pixel clipping of a CCD. The camera signal processing control portion 11 corresponds to a vibration shake correction portion of the present invention. The scope of the present invention is not limited thereto, but vibration shake may be optically corrected by adjusting positions or angles of the lenses of the lens unit 7.

According to the endoscope apparatus 1 of the embodiment of the present invention, the vibration generating device 4 is provided on the camera unit portion 3 to reduce the cost and size of the scope portion 2 and increase a defogging effect.

Specifically, in this embodiment, when the vibration generating device 4 mounted to the camera unit portion 3 generates vibration, the scope portion 2 vibrates at its natural frequency along its entire length. Thus, the vibration of the vibration generating device 4 can be sufficiently transmitted to the imaging window 5 through the scope portion 2 to defog the imaging window 5. Thus, there is no need for providing the vibration generating device 4 in the scope portion 2 as in the conventional example, thereby reducing the size of the scope portion 2. Generally, in surgery using a laparoscope, an incision of several cm is made beside a belly button to insert a scope portion 2. Thus, a smaller scope portion 2 causes a smaller incision wound in surgery to place a lighter burden on a body.

In this embodiment, electric power may be easily supplied or controlled from outside to the vibration generating device 4 mounted to the camera unit portion 3. Thus, there is no need for passing a wire for supplying or controlling electric power through the scope portion 2 and for providing measures to prevent leakage of electricity in a body cavity as in the conventional example. This can reduce the cost and size of the scope portion 2. The vibration generating device 4 is mounted to the camera unit portion 3, and thus the vibration generating device 4 can easily generate strong vibration to provide a sufficient defogging effect.

In this case, there is no need for providing the vibration generating device 4 in the scope portion 2, thereby reducing the size of the scope portion 2. There is no need for passing a wire through the scope portion 2 and for providing measures to prevent leakage of electricity in the body cavity. This can reduce the cost and size of the scope portion 2.

The vibration generating device 4 is mounted to the camera unit portion 3, and thus the vibration generating device 4 can easily generate strong vibration to provide a sufficient defogging effect. For the endoscope apparatus 1 including a replaceable scope portion 2, it is only necessary to mount the vibration generating device 4 to the camera unit portion 3. Thus, the scope portion 2 that is not exclusive can be used as it is, thereby providing high flexibility in selection of the scope portion 2.

In this embodiment, the shake of the obtained image that occurs while the vibration generating device 4 is generating vibration is reduced by the vibration shake correction. This allows quick confirmation of whether defogging is completed or not, thereby increasing surgery efficiency.

The embodiment of the present invention has been described by way of example, but the scope of the present invention is not limited thereto, and changes and modifications may be made according to objects within the scope described in the claims.

In the above example, the endoscope apparatus described is a medical endoscope for imaging the inside of the abdominal cavity during surgery. However, the scope of the present invention is not limited thereto. For example, the endoscope apparatus may be an industrial endoscope for imaging high temperature and humid space in a production line of a plant.

The preferred embodiment of the present invention probable at the present time has been described, but it should be understood that various modifications may be made to this embodiment, and the appended claims are intended to cover all such modifications falling within the true spirit and scope of the present invention.

INDUSTRIAL APPLICABILITY

As described above, the endoscope apparatus according to the present invention can reduce the cost and size of a scope portion and has a high defogging effect, and is useful for use as a medical or industrial endoscope.

The invention claimed is:

1. An endoscope apparatus comprising:
   a rigid scope portion having an imaging window at a front end thereof;
   a camera unit portion which is mounted to a root end of said rigid scope portion and has an image pickup portion which can obtain an image through said imaging window; and
   a vibration generating device which is mounted to said camera unit portion and provides vibration to said imaging window through said camera unit portion.

2. The endoscope apparatus according to claim 1, further comprising a vibration shake correction portion that corrects vibration shake of an image obtained by said image pickup portion while said vibration generating device is providing vibration to said rigid scope portion.

3. An endoscope camera apparatus used in an endoscope apparatus according to claim 1, wherein the endoscope camera apparatus is mounted to a root end of a rigid scope portion, and a vibration generating device can be mounted to the endoscope camera apparatus.

4. The endoscope apparatus of claim 1, wherein the vibration generating device is mounted on an outer surface of the camera unit portion without providing a vibration generating device in the rigid scope portion.

5. The endoscope apparatus of claim 1, wherein the vibration generating device is mounted on an outer surface of the camera unit portion without passing a wire through the rigid scope portion.

6. The endoscope apparatus of claim 1, wherein the vibration generating device is mounted on an outer surface of the camera unit portion without providing a measure to prevent leakage of electricity.

7. The endoscope apparatus of claim 1, wherein the vibration generating device provides vibration to said imaging window through said camera unit portion and said rigid scope portion.

8. A method of defogging an imaging window of an endoscope apparatus comprising:
   providing the endoscope apparatus having a rigid scope portion having an imaging window at a front end thereof; a camera unit portion having an image pickup portion which can obtain an image through said imaging window; and a vibration generating device which is mounted on an outer surface of said camera unit portion, one end of the rigid scope portion being mounted to the camera unit portion and the other end of the rigid scope portion having the imaging window;
   generating vibration by said vibration generating device; and
   transmitting the vibration to said imaging window through the camera unit portion.

9. The method of claim 8, wherein the method does not comprise providing a vibration generating device in the rigid scope portion.

10. The method of claim 8, wherein the method does not comprise passing a wire through the rigid scope portion.

11. The method of claim 8, wherein the method does not comprise providing a measure to prevent leakage of electricity.

12. The method of claim 8, wherein the vibration generating device provides vibration to said imaging window through said camera unit portion and said rigid scope portion.

* * * * *